(12) United States Patent
Raza et al.

(10) Patent No.: US 11,033,070 B2
(45) Date of Patent: Jun. 15, 2021

(54) DEVICE FOR PREVENTING AND TREATING FOOT AND LEG ULCERS

(71) Applicants: Maryam Raza, Dallas, TX (US); Richard C Galperin, Dallas, TX (US); Ahmad Masud Choudri, Dallas, TX (US); Samuel Galperin, Boynton Beach, FL (US)

(72) Inventors: Maryam Raza, Dallas, TX (US); Richard C Galperin, Dallas, TX (US); Ahmad Masud Choudri, Dallas, TX (US); Samuel Galperin, Boynton Beach, FL (US)

( * ) Notice: Subject to any disclaimer, the term of this patent is extended or adjusted under 35 U.S.C. 154(b) by 0 days.

(21) Appl. No.: 15/932,634

(22) Filed: Mar. 29, 2018

(65) Prior Publication Data

US 2019/0297992 A1 Oct. 3, 2019

(51) Int. Cl.
*A43B 7/14* (2006.01)
*A43B 3/12* (2006.01)
*A43B 13/12* (2006.01)
*A43B 13/38* (2006.01)
*A43B 3/24* (2006.01)
*A43B 13/14* (2006.01)

(52) U.S. Cl.
CPC ............. *A43B 7/147* (2013.01); *A43B 3/128* (2013.01); *A43B 13/12* (2013.01); *A43B 13/386* (2013.01); *A43B 3/246* (2013.01); *A43B 7/1415* (2013.01); *A43B 7/1465* (2013.01); *A43B 13/146* (2013.01)

(58) Field of Classification Search
CPC ..... A43B 7/145; A43B 7/1415; A43B 7/1465; A43B 3/128; A43B 13/12; A43B 13/386; A43B 13/246; A43B 3/246
See application file for complete search history.

(56) References Cited

U.S. PATENT DOCUMENTS

| 4,217,706 | A | * | 8/1980 | Vartanian | A43C 11/008 36/110 |
|---|---|---|---|---|---|
| 5,164,878 | A | * | 11/1992 | Hauser | A43B 7/142 36/155 |
| 5,329,705 | A | * | 7/1994 | Grim | A43B 1/0009 36/110 |
| 7,231,728 | B2 | | 6/2007 | Darby | |
| 8,056,149 | B2 | | 11/2011 | Duclos | |
| 8,201,346 | B2 | | 6/2012 | Darby | |
| 8,323,282 | B2 | * | 12/2012 | Taylor | A61B 17/62 36/110 |
| 9,198,801 | B2 | | 12/2015 | Weston | |
| 9,387,125 | B1 | | 7/2016 | Duda | |
| 2002/0069555 | A1 | * | 6/2002 | Sinaie | A43B 7/1425 36/43 |
| 2003/0195449 | A1 | * | 10/2003 | Coleman | A61F 13/085 602/75 |

(Continued)

*Primary Examiner* — Jila M Mohandesi
(74) *Attorney, Agent, or Firm* — Maqsood Ahmad

(57) ABSTRACT

A device is configured to treat ulcers/chronic wounds. First, and intermediate insoles are constructed from including the semi-compressed felt. A third sole serving as the base of the device is made constructed from including Ethylene Vinyl Acetate EVA. A cavity with beveled edge in the first insole is configured to over-lap the chronic wounds or ulcerations. The cavity channels the drainage or extrude from the ulcerations to the intermediate insole where it is absorbed.

8 Claims, 5 Drawing Sheets

(56) References Cited

U.S. PATENT DOCUMENTS

| | | | | |
|---|---|---|---|---|
| 2004/0045195 A1* | 3/2004 | Long | ............ | A43B 1/0009 |
| | | | | 36/88 |
| 2005/0166425 A1* | 8/2005 | Seiter | ............ | A43B 7/22 |
| | | | | 36/44 |
| 2006/0156456 A1* | 7/2006 | Teixeira | ............ | A41B 11/006 |
| | | | | 2/239 |
| 2010/0324455 A1* | 12/2010 | Rangel | ............ | A43B 7/147 |
| | | | | 600/592 |
| 2011/0214315 A1* | 9/2011 | Mayer | ............ | A61F 5/14 |
| | | | | 36/140 |
| 2011/0264023 A1* | 10/2011 | Devito | ............ | A61F 5/0111 |
| | | | | 602/27 |
| 2015/0075030 A1* | 3/2015 | Walborn | ............ | A43B 1/0009 |
| | | | | 36/44 |
| 2017/0273851 A1* | 9/2017 | Larmer | ............ | A61F 13/085 |
| 2019/0008693 A1* | 1/2019 | Malinsky | ............ | A61F 13/08 |
| 2019/0373984 A1* | 12/2019 | Wijesundara | ............ | A61F 5/14 |

* cited by examiner

DEVICE FOR PREVENTING AND TREATING FOOT AND LEG ULCERS

CROSS-REFERENCE TO RELATED APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document includes material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the present invention generally, are related to healing/treatment of the foot ulcerations and the chronic wounds. More specifically, this invention is related to a device, healing shoe and a compression sock detachably attached to the device to treat the foot and leg ulcerations or the chronic wounds.

BACKGROUND OF THE INVENTION

The foot and leg ulcerations generally, are caused by normal pressure, shear force or by the combined effect of normal pressure and shear loadings. The skin weakened by pressure ischemia may be more susceptible to friction, and the two will act together to hasten skin breakdown. The foot and leg ulcerations are the most prevalent chronic wounds in about 2% of the adult population in the United States. The main causes of the foot and leg ulcerations are diabetes and arterial insufficiency. Venous ulcerations account for about 80% of all the foot and leg ulcerations are the result of venous hypertension. The studies show that about 70% of the foot and leg venous ulcerations remain unhealed after about 12 weeks of treatment. The foot and leg ulcerations treatment costs the United States about over one billion dollars per year and have a significant impact on the patient's quality of life.

The biology of chronic venous and diabetic ulcerations is quite different from the acute wounds. In an acute wound the initial fibrin clot provides hemostasis and the platelets release cytokines, growth factors, and recruit inflammatory cells. The inflammatory cells include neutrophils and macrophages to eradicate bacteria. At the leading edge of the wound are the proteases cut through the fibrin clot. The Matrix Metalloproteinases (MMP) is up and regulated by the keratinocytes to cut a path through the matrix proteins to allow the keratinocyte to advance and close the wounds. The MMP-9 (gelatinase B) cuts through the basal lamina collagen (type IV) and anchoring collagen (type VII) to allow the keratinocytes to advance and close the wound. Once the keratinocytes cover the wound, the wound is re-epithelized, the basal lamina is reestablished and the MMP-9 is shut off.

However, in ulcerations and chronic wounds, MMP-9 is not shut off. The elevated levels of this protease continue to destroy the wound matrix, which is produced to heal the wounds. The level of MMP-9 of ulcerations and chronic wounds can be five times of its level in an acute wound. The MMP-9 is the major protease present in the chronic venous stasis and decubitus ulcerations.

The tissue inhibitor of metalloproteinase (TIMP-1) is absent from the ulcerations and chronic wounds and it also decreases with age. The ulcerations and chronic wounds also become colonized with bacteria. The bacterial colonies produce a biofilm which enables the bacteria to act as multicellular organism. The biofilm protects the bacteria from the host immune system and all antibiotics. The bacterial biofilm gains nutrients from its own protease, which are similar to the host MMP-9. The biofilm then protects the bacteria from the host immune system and all antibiotics. Thus, in ulcerations and chronic wounds, the bacterial biofilm and the host both produce proteases which are responsible for the degradation of the factors responsible for the wound healing.

In the past, many techniques and devices including, but not limited to, multilayer socks, socks with electric impulses, and socks doped with metallic powder such as AgNP (Silver Nanoparticles) powder have been used with limited degree of success in the treatment of the foot and leg ulcerations. Each technology has been identified with advantages and disadvantages. For example, AgNP particles have been found to adversely affect various body organs such as liver and kidneys.

Various techniques or devices have been developed with limited success for healing or treating the foot and leg ulcerations and the chronic wounds. For example: U.S. Pat. No. 9,387,125 titled "A sock for treating of foot and leg wounds, method of use and its manufacture discloses," The Improved Sock is made of yarns knitted into a foot and calf, with graduated compression on an individual's foot from the foot to the calf. The yarns can include wool and alpaca fibers. A substantial proportion of wool and/or alpaca are on the inside of the sock so as to be in direct contact with the skin and wound. The Improved Sock provides absorption and wicking of inflammatory mediators, bacteria and biofilm and necrotic exudate from the foot and leg. The Improved Sock has AgNP shapes electrostatically bonded to the yarn. At least 30% of the mass of the AgNP shapes attached to the fibers have a shape selected from the group consisting of truncated triangular plates (a triangle with the corners rounded off), triangular prisms, discs and combinations of two or more of them. The Improved Sock functions as a unique wound dressing with the sock in direct contact with the wound." Note/Analysis: The sock is in direct contact with the wound, particularly at the bottom of the foot, and there is no pressure off-loading of the wound. Additionally, the anti-inflammatory, anti-fungal, and anti-bacterial AgNP particles (silver nanoparticles) adversely affect liver, kidneys and other vital organs of the body. It is the inflammation which is mainly responsible for prolonged healing of diabetic and chronic wounds. However, instead of offloading the diabetic and chronic wounds, using AgNP particles for controlling inflammation of these wounds is not successful.

Another prior art, U.S. Pat. No. 8,201,346 titled: Medical shoe system discloses, "A system, method, and apparatus for treating a foot using a medical shoe and interchangeable insoles. A plurality of interchangeable insoles is provided, including a surgical insole and a wound care insole. The surgical insole provides rigidity for a patient's foot. The surgical insole comprises a first upper layer and a rigid second lower layer. The wound care insole offloads weight from a wound region on the foot. The wound care insole comprises a first upper layer of stretchy, thin film, a second, middle, layer that is moldable, and a third, lower layer that is spongy and provides support." Note/Analysis: The above mentioned prior art does not engage the same methodology as proposed in the present invention. There is no use of compression sock which enhances blood flow in the foot and the shank/calf and significantly helps in treating the foot and leg ulcerations at a much faster pace. Unlike the proposed invention, there is no direct offloading of the wounds, and thus there is no appreciable reduction in ulcerations or wounds at a rapid pace.

Another prior art, U.S. Pat. No. 8,056,149 titled: A combination sock and shoe discloses, "A combination sock and shoe includes a shoe sole, an exterior sock that is secured to the shoe sole, an intermediate sock positioned inside the exterior sock, and an interior sock positioned inside the exterior sock and inside the intermediate sock. The intermediate sock is constructed as an anklet having an elastic ankle opening. The exterior and interior socks conceal the intermediate sock from view by sandwiching the intermediate sock between them. When a wearer's foot is inserted into the combination sock and shoe, the elastic ankle opening of the intermediate sock securely engages around the ankle of the wearer's foot and holds the wearer's foot to the shoe sole, thereby preventing the shoe sole from separating away from the heel of the wearer's foot during walking." Note: This prior art does not disclose that it is a wound treating shoe. It is simply a walking shoe that holds the heel of the foot in place.

Another prior art, U.S. Pat. No. 9,198,803 titled, "Dressing device for offloading and treating an ulcer, discloses, "A dressing device has a device body, a bore extending into an inner surface of the device body, and a biasing element positioned within the bore for biasing the dressing element against the ulcer. The device body functions to offload pressure from an ulcer of a patient. The biasing element functions to support a dressing element against the ulcer to medicate the ulcer, and to prevent the formation of proud flesh."
Note:/Analysis: the device described in the above cited prior art is a dressing but not a shoe. There is no mention of the compression sock, and its usefulness in treating the ulcerations and the chronic wounds.

Another prior art, U.S. Pat. No. 7,231,728 titled: "healing shoe or sandal, discloses, "A medical shoe for use in supporting a patient's foot and a method of using same, the medical shoe comprising an out sole, an upper assembly secured to and partially surrounded by the out sole and an insole assembly substantially enclosed by the outsole and the upper assembly. The outsole having a base portion generally corresponding with the plantar aspect of a human foot and of varying thickness and having a substantially rectangular opening in a top surface of the base portion thereof adapted for accommodating a metatarsal shank. The out sole having a circumferential counter portion extending upward circumferentially from the top surface of the base portion thereof around the base portion of the outsole thereby providing a cavity in the outsole. The upper assembly adapted to surround at least the heel, sides and dorsal portions of the human foot. The upper assembly attached to the top surface of the base portion of the outsole and the circumferential counter of the outsole, and extending in a dorsal direction from the top surface of the base portion of the outsole along the circumferential counter. The insole assembly having a plurality of insole layers disposed in the outsole cavity and surrounded by the upper assembly and the outsole circumferential counter. The plurality of insole layers provided to include a first insole layer, a second insole layer a third insole layer and a fourth insole layer wherein the first and second layers are an Ethyl Vinyl Acetate (EVA) material and the second layer has a durometer less than the first layer, the third layer is a Peron material with a durometer less than the second layer, and the fourth layer is an EVA material with a durometer less than the third layer, and the first, second, third, and fourth layers may be assembled in any order as determined by a health care provider." Note/Analysis: The above referenced prior art claims to provide an easy to use healing shoe or sandal and an effective method to offload pressure from a particular area of the plantar aspect (bottom) of the human foot by using alterable insole or insole layers of varying densities and degrees of firmness which fit into an area surrounded by a circumferential counter, in order to hold the insole layers in position. However, the referenced prior art solely depends on the insoles positioning and placement to achieve offloading pressure on specific foot areas. There is no mention of cutting the sole to accommodate ulcerations for offloading or redirecting pressure, and using compression sock for efficient and enhanced recovery of the ulcerations, or wounds.

Treatment of the foot and leg ulcerations and chronic wounds usually requires months for a successful resolution/recovery. Unlike the present invention, the efficacy of the techniques/devices used in the prior art still leave much to be desired. For example, none of the above disclosed prior art, addresses how to offload pressure from the ulcerations and chronic wounds using top insole with a cavity in the insole in alignment with the ulcerations or wounds, and using the compression sock for relatively faster and efficient recovery of ulcerations and chronic wounds. Using the present invention, the recovery time for ulcerations has been documented about 3 weeks.

In the present invention a plurality of insoles with a beveled cavity in the first insole, an intermediate insole and sock equipped with a zipper is devised in treating the foot and leg ulcerations. A clinical study by the wound care doctors and specialists shows that this combination of unique device and methodology heals the foot and leg ulcerations relatively much quicker approximately 3-4 weeks as compared to 3 months as stated in the prior art. The remarkable results justify the need for this new and unique invention, device and methodology/method.

SUMMARY OF THE INVENTION

To achieve the forgoing and other objectives in accordance with the purpose of the present invention, a device and process is devised for the treatment of the foot and leg ulcerations and chronic wounds. It takes into consideration and understanding the role of various factors such as body weight (pressure) of the patient, friction, shear force and other factors which contribute to varying degrees causing inflammation to the foot and leg ulcerations and chronic wounds while walking.

It is to be understood that the present invention is not limited to the particular methodology, system, techniques, uses, and applications, described herein, as these may vary. It is also to be understood that the terminology used herein is for the purpose of describing particular embodiments only, and is not intended to limit the scope of the present invention in any manner.

In one embodiment of the present invention, the healing device/shoe and third sole (base of the shoe) is made from including, but not limited to Ethylene Vinyl Acetate (EVA). An intermediate insole which is a second insole made from including, but not limited to semi-compressed felt. A top insole is the first insole having a cavity created in it, and is also made from including, but not limited to semi-compressed felt. A compression sock is equipped with zipper to facilitate placement of the intermediate, and the first insoles with the cavity, in alignment with the bottom of the foot with ulceration. The zipper can be opened and closed approximately and it nears the digits of the foot. The cavity in the first insole surrounds the ulcerations or wounds at the bottom of the foot. This significantly facilitates offloading the plantar pressure from the ulcerations and chronic wounds. The top edges of the cavity are beveled, and this reduces the stresses associated with sharp edges of the cavity. The foot is placed inside the sock on the first insole in such a manner that the foot ulcerations and chronic wounds remain uncovered. If there is any drainage or extrude from the ulcerations or wounds, it is collected through the cavity by the intermediate insole which is made from the semi-compressed-felt, and it is fluid absorbent as well. The semi-compressed felt also provides good aeration to the ulcerations and the chronic wounds. The bottom of the sock is detachably attached to the top surface of the third sole with low adhering adhesive. The compression sock is uniform in terms of pressure as needed within the specifications. The strength of compression sock varies from 10-50 mmHg.

In another embodiment of the present invention, the cavity in the first insole redirects the loading from foot plantar pressure and helps the ulcerations from inflammation standpoint, which in turn facilitates to quick and affective recovery of the ulcerations/wounds. It is emphasized that redirecting the foot plantar pressure and controlling/alleviating the inflammation of the ulcerations is the key in expediting recovery/treatment of the ulcerations and chronic wounds.

In another embodiment of the present invention, the semi-compressed-felt provides adequate aeration, oxygen, to the ulcerations and chronic wounds by virtue of the material being used, and this promotes significantly early recovery as compared to prolonged recovery using the devices and techniques as stated in the prior art. The semi-compressed felt also provides comfort to the ulcerations and wounds by the cushioning effect. It is to be pointed out that the semi-compressed material is self-aerating.

In another embodiment of the present invention, the zipper incorporated to the compression sock provides ease and comfort to the ulcerations and wounds and to the patient. The patient, with the zipper in open position, is able to place the insoles (first insole with the cavity, and the intermediate insole) and the foot with ulcerations or wounds at the bottom within the compression sock without rubbing or scratching the ulcerations or wounds.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE DRAWINGS

Figure 1:
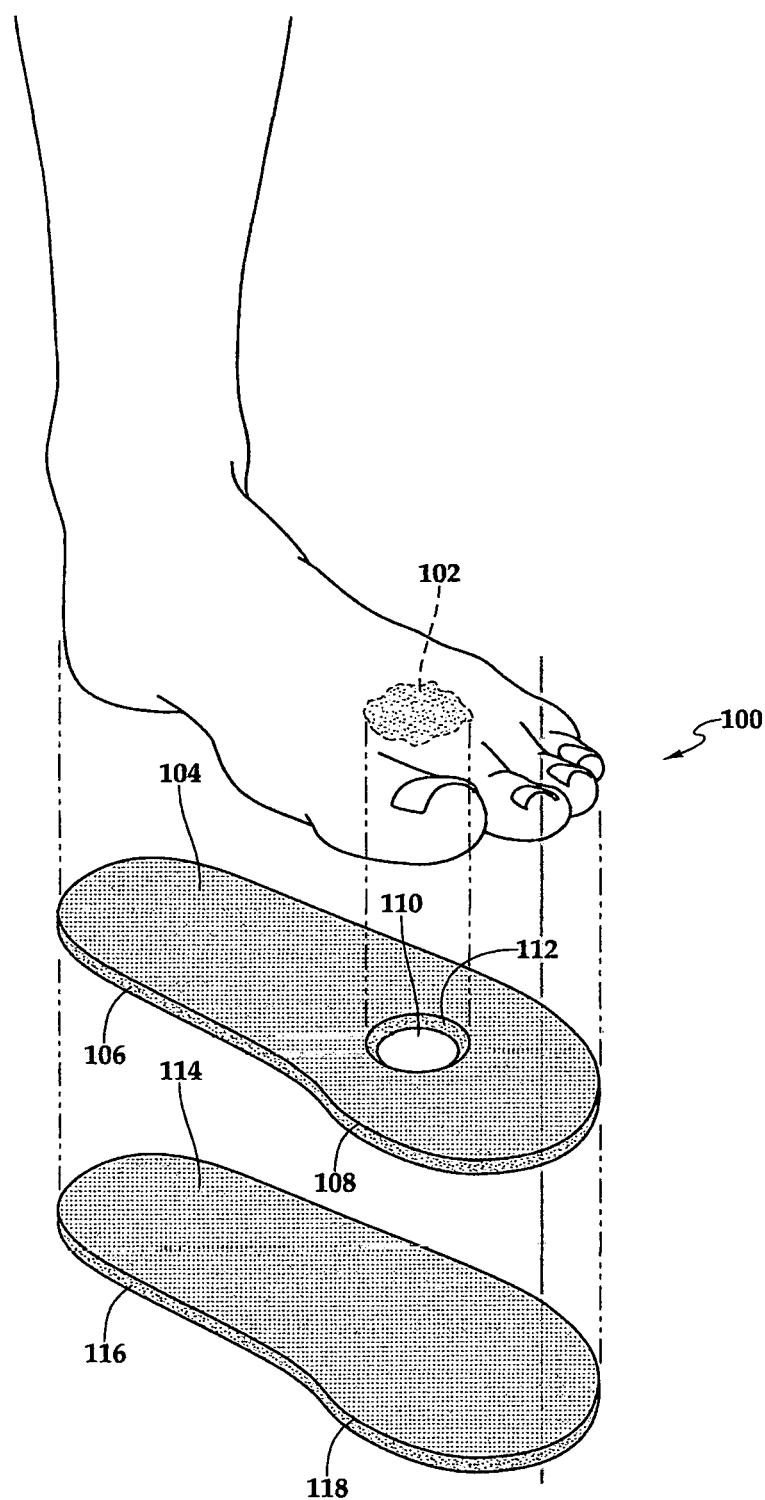
FIG. 1 depicts an illustration 100 of various components of the device, and methodology in accordance with an embodiment of the present invention.

The present invention is best understood by reference to the detailed figures and description set forth herein.

Embodiments of the present invention are discussed below with reference to the Figures. However, those skilled in the art will readily appreciate that the detailed description with respect to these figures is for explanatory purposes as the invention extends beyond these limited embodiments. For example, it must be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, in another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments as illustrated in the accompanying drawings.

The present disclosure's variations and modifications will be apparent to persons skilled in the art. Such variations and modifications may involve equivalent and other features which are already known in the art, and which may be used instead of or in addition to features already described.

Features described in the context of separate embodiments may also be provided in combination in a single embodiment. Conversely, various features which are, for brevity, described in the context of a single embodiment, may also be provided separately or in any suitable sub-combination. The Applicants hereby give notice that new Claims may be formulated to such features and/or combinations of such features during the prosecution of the present Application or of any further Application derived therefrom.

References to "one embodiment," "an embodiment," "exemplary embodiment," "various embodiments," etc., may indicate that the embodiment(s) of the present invention described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is well known to those skilled in the art that several careful considerations and compromises typically must be made when designing for the optimal manufacture of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(s), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be further understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

It is specifically emphasized that any teaching or combination of teachings, any novel feature, or any novel combination of features including the novel processing mechanism, or any combination of novel processing mechanisms for the device, system, methodology and process, in accordance with an embodiment of the present invention, is clearly distinguished from the prior art as cited above in paragraphs [0011], [0012], [0013], [0014], and [0015] either alone or in combination do no teach all the features of the present invention. There are no findings in the prior art that teach, or suggest a system or a method using a cavity in the top insole in alignment with the ulceration, optional use of medication for the ulcerations/wounds, a compression sock with variable compression for treating the ulcerations/chronic wounds combined together quickly (with treatment healing time of about 4 weeks) and affectively.

It is further emphasized that the present invention significantly differentiates itself from the prior art as shown in the analysis of the prior art as provided in the prior art review.

To achieve the forgoing and other objectives in accordance with the purpose of the present invention, a device and methodology/process for treating the ulcerations/chronic wounds is presented in the present invention. It is to be further understood that the present invention is not limited to the particular methodology, system, techniques, uses, and applications, described herein, as these may vary. It is also to be understood that the terminology used herein is used for the purpose of describing particular embodiments only, and is not intended to limit the scope of the present invention in any manner or fashion. The present invention is illustrated by way of example, and not by way of limitation, in the figures of the accompanying drawings in which like reference numerals refer to similar elements and in which:

FIG. 1 is an illustration of exemplary device/article of manufacture schematic 100, showing an ulceration or chronic wound 102 at the bottom of the foot. The ulceration/chronic wound 102 may have any configuration. The first insole 104 constructed from semi-compressed-felt having a bottom surface 106 and a top surface 108. The thickness of the insole 104 is about ½-¾ of an inch. The bottom surface 106 of the first insole 104 is coated with a low adhering adhesive protected by a polyurethane film. The low adhering adhesive includes, but not limited, to acrylic, polyurethane, or silicone adhesive. The low adhering adhesive and the polyurethane film are not shown in the drawings. The first insole 104 also has a cavity 110 configured in it. The cavity 110 is carved in alignment with the ulcerations/wounds 102. The beveling 112 is employed for an effective and uniform redistribution of foot loading and consequently less stresses to the ulcerations/chronic wounds 102. The size of the cavity 110 is about ⅛ of inch bigger than the ulceration and/or wound 102 on the bottom of the foot. The cavity 110 overlaps the ulcerations 102. The intermediate insole 114 is also constructed from semi-compressed-felt. The intermediate insole having the bottom surface 116 and the top surface 118. The bottom surface of the second insole (intermediate insole) 114 is coated with a low adhering adhesive and it is protected by polyurethane film. The low adhering adhesive includes, but not limited, to acrylic, polyurethane, or silicone adhesive. The low adhering adhesive and the polyurethane film are not shown in the drawings. The thickness of the intermediate insole 114 is about ½ of an inch in thickness. The first insole 104 and the intermediate insole 114 are capable of having the self-aeration which is essential in providing oxygen to the ulcerations and chronic wounds for affective and quick healing.

Figure 2:
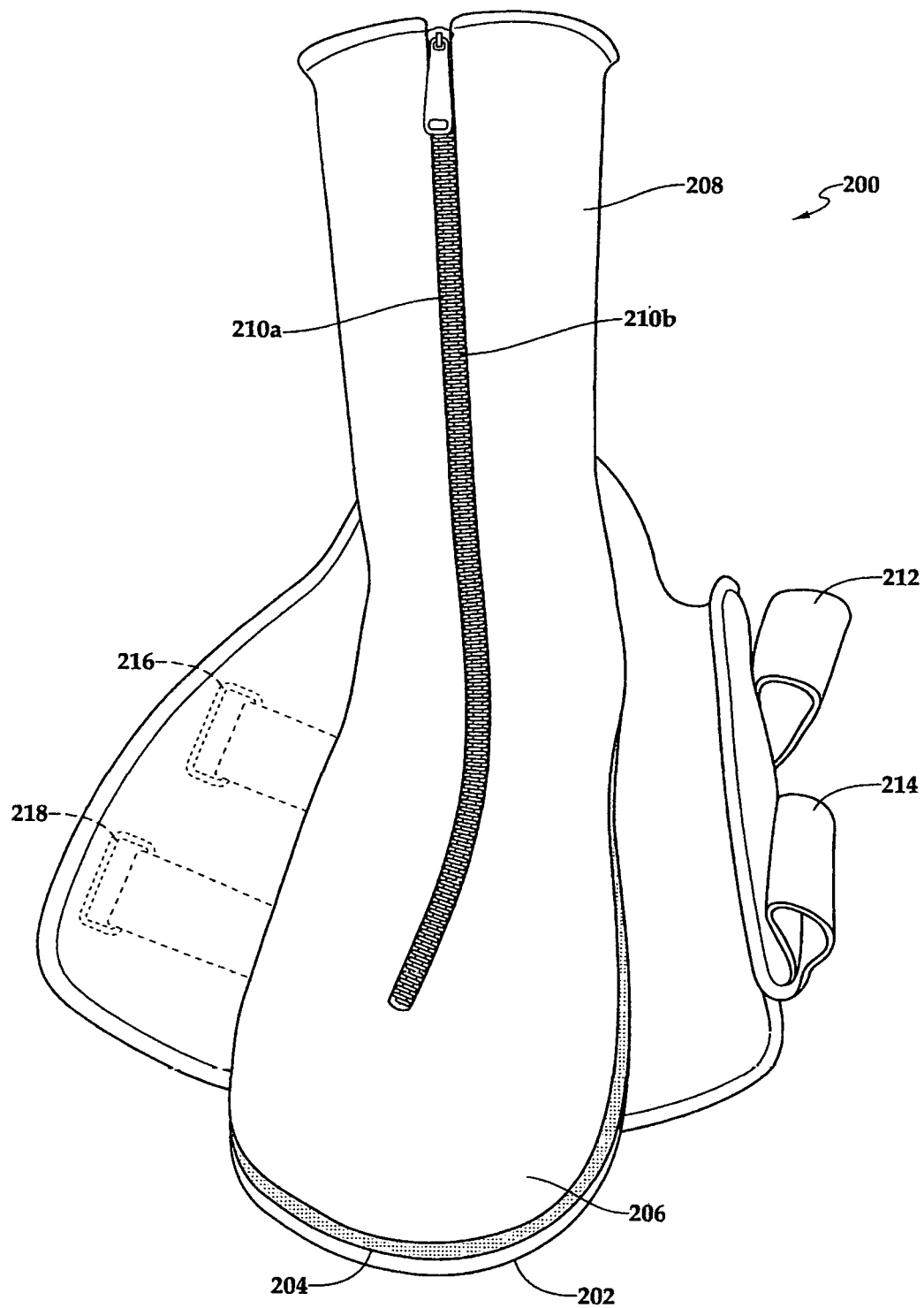
FIG. 2 is an illustration of exemplary schematic 200 showing a compression sock with or without graduation in terms of compression and equipped with a zipper in the closed position, in accordance with an embodiment of the present invention.

FIG. 2 is an illustration of exemplary device/article of manufacture schematic 200. The device is showing the third sole 202 as the integral part (molded) is permanently attached to the device (healing shoe). The device having a bottom surface 204 and a top surface 206. The bottom surface 204 is serrated for traction during walking. The top surface 206 is treated with the low adhering adhesive, not shown in the FIG. 2. The bottom of the compression sock 208 is coated with the low adhering adhesive, and placed on the top surface 206 coated with the low adhering adhesive (not shown in FIG. 2). The compression sock 208 is detachably attached to the top surface 206 of the device. The compression sock 208 is equipped a zipper 210(a) 210(b). The zipper 210(a) and 210(b) is shown in the closed position. The straps 212, 214, 216 and 218 are used to close, open or secure the device 200.

Figure 3:
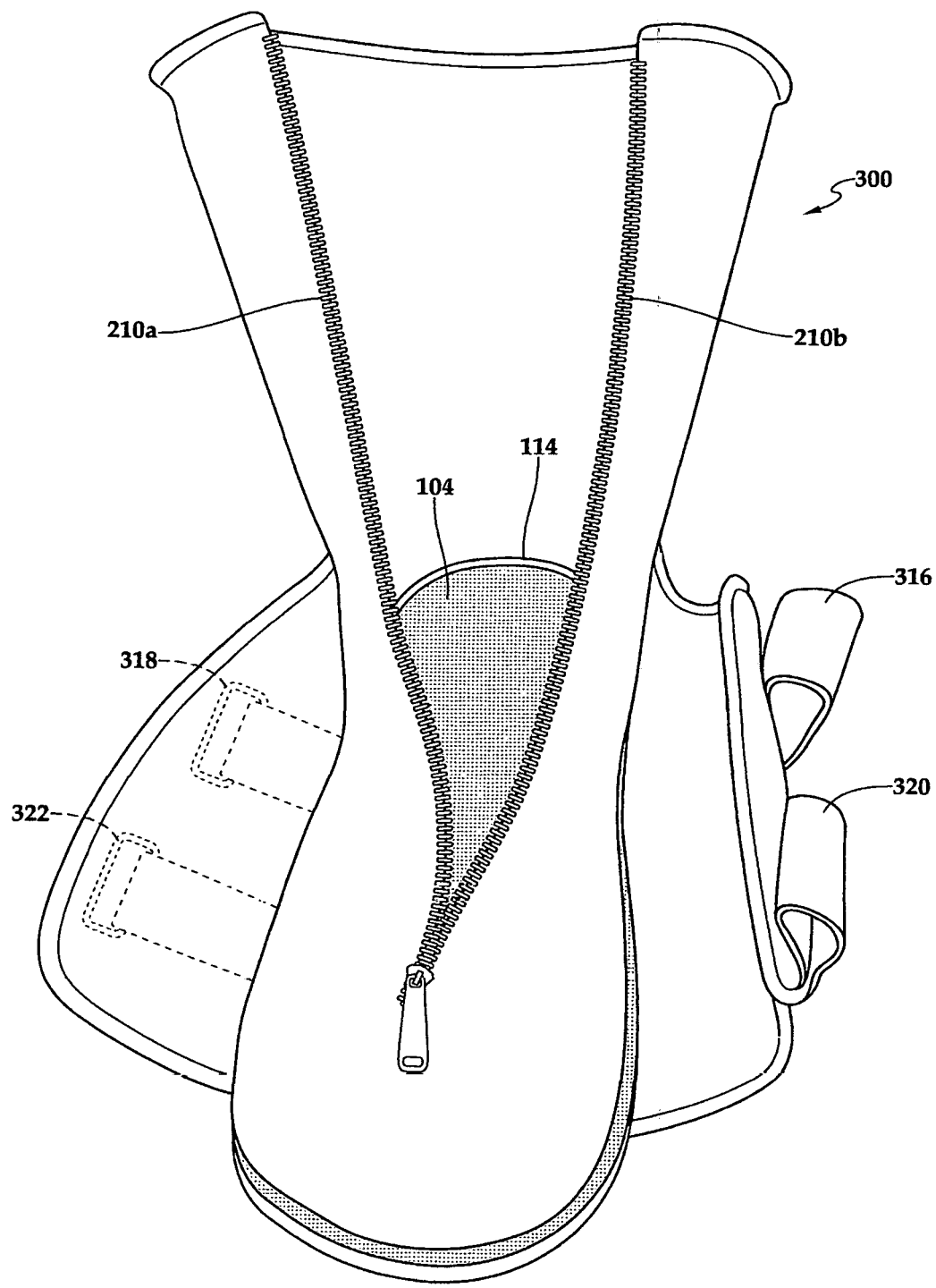
FIG. 3 is an illustration of the exemplary schematic 300. The zipper in the open position and the insoles placed inside the compression sock, in accordance with the embodiment of the present invention.

FIG. 3 is an illustration of exemplary device/article of manufacture schematic 300. The zipper 210(a) and 210(b) shown in FIG. 2 is in the open position. The first insole 104 and the intermediate insole 114 as shown in FIG. 1 are placed inside the compression sock 208. The first insole 104 has cavity 110 with the beveling 112 shown in FIG. 1, is placed on the top surface 114 of the intermediate insole. The bottom surface of the first insole 106 and, the top surface 114 of the intermediate insole coated with the low adhering adhesive are mated together and detachably attached. Prior to mating the protective film is removed from the first insole 104 and the intermediate insole 114.

Figure 4:
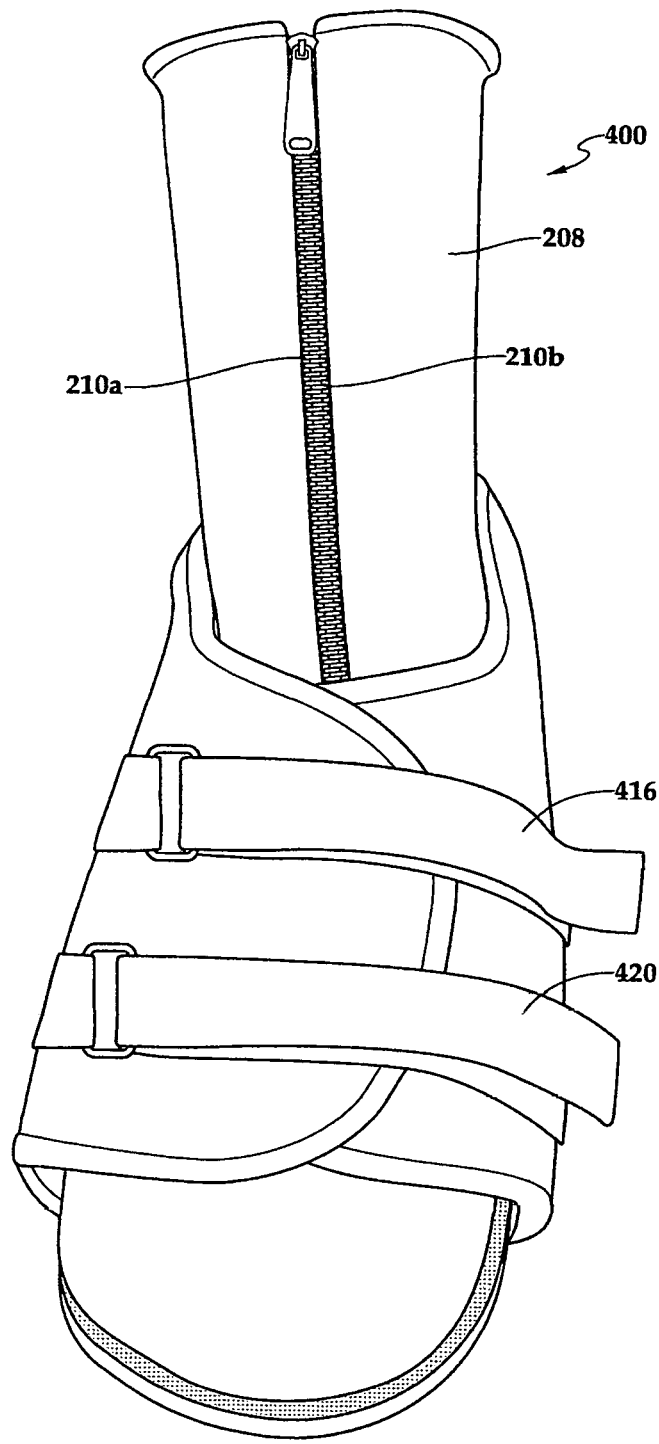
FIG. 4 is an illustration on the exemplary schematic 400 and depicts a comprehensive view of the device, zipper in the closed position, the foot ulcerations along with the first insole and the intermediate insole, is in accordance with an embodiment of the present invention.

FIG. 4 is an illustration of exemplary device/article of manufacture 400. The compression sock 208 as it is previously shown in FIG. 2 is closed by mating 210a and 210b. Prior to closing by mating 210a and 210b, the first insole 104 is placed on the intermediate insole 114 then both the insoles are placed inside the compression sock 208, followed by the foot with ulceration/chronic wound 102 is inserted inside the compression sock in a manner that the cavity 110 with beveling 112 in the first insole surrounds the ulcerations/chronic wounds 102. Finally, the foot with ulcerations/chronic wounds 102, the first insole 104 and the intermediate insole 114 and the compression sock 208 which is detachably attached with the third sole 206 are secured with the straps 416 and 420 as shown in FIG. 2-4.

Figure 5:
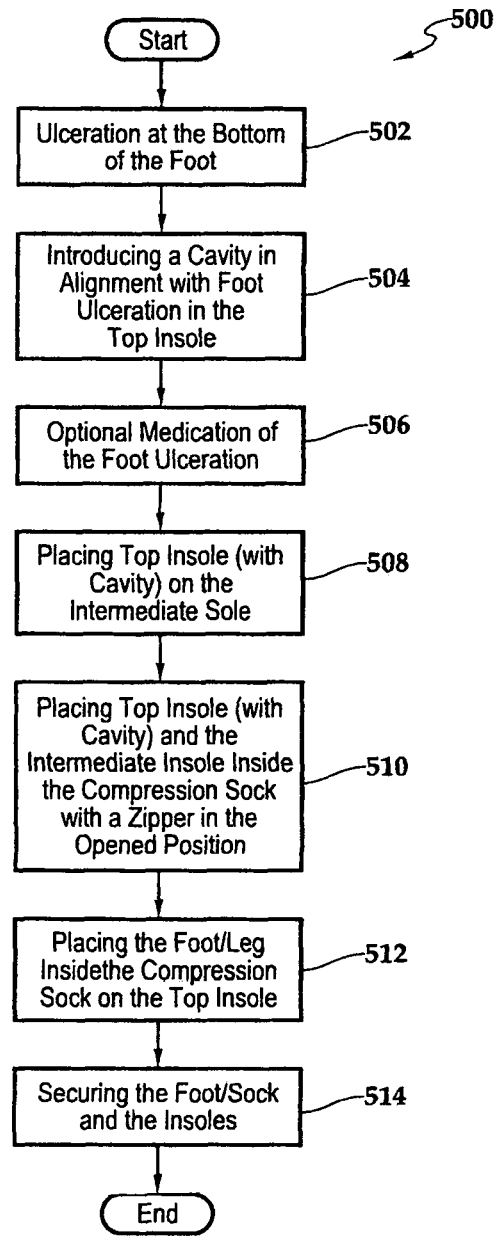
FIG. 5 is an illustration of exemplary flow chart 500 depicting the device, methodology for constructing and using the device, in accordance with an embodiment of the present invention.

FIG. 5 is a flow chart of an illustration of exemplary device/article of manufacture 500. It shows ulcerations/chronic wounds represented by the step 502 at the bottom of the foot 102. A cavity 110 with the beveling 112 is shown in the first insole 104 in FIG. 1 is represented by the step 504. The beveling 112 is beveled on top edges of cavity to reduce the amount of residual stress associated with the sharp edges of the cavity 110. The residual stresses transferred to the ulceration/chronic wound prolong the healing process. Optional medicating with the medication of choice of the foot ulcerations/chronic wounds 102 facilitates in quick healing as represented by the step 506. The first insole 104 is placed on the second or intermediate insole 114. The first insole 104 with the cavity 110 in it is always in alignment with the ulceration/chronic wound 102 on the bottom of the foot as shown in FIG. 1, and is represented by the step 508. The first insole 104, the intermediate insole 114 are first placed inside the compression sock as shown in FIG. 3, and followed by the foot with ulcerations/chronic wounds 102 is inserted in the compression sock 208 in such a manner that the cavity 110 surrounds the ulcerations/chronic wounds as shown in FIG. 1-2 and represented in 510 and 512. The first insole 104, the intermediate or second sole 114 and the foot with ulcerations/chronic wounds 102 are closed inside the compression sock 208 by closing the zipper 210a and 210b. Finally the entire assembly is secured in the device by the straps as it is represented in 514.

Having fully described at least one embodiment of the present invention, other equivalent or alternative methods of providing a method and device for the multilayer dressing will be apparent to those skilled in the art. The invention has been described above by way of illustration, and the specific embodiments disclosed are not intended to limit the invention to particular forms disclosed. For example, the particular implementation of the method and system may vary depending upon a particular type of application for which it is to be used. However, similar alternatives may be used, for example; refining or improving the present invention (implementations of the present invention) is contemplated as within the scope of the present invention. The invention is thus, to cover all modifications, equivalents, and alternatives falling within the spirit and scope of the following claims.

Although Claims have been formulated in this Application to particular combinations of features, it should be understood that the scope of the disclosure of the present invention also includes any novel feature or any novel combination of features disclosed herein either explicitly or implicitly or any generalization, whether or not it relates to the same invention as presently claimed in any Claim and whether or not it mitigates any or all of the same technical problems as does the present invention.

Claim elements and steps may have been numbered and/or lettered solely as an aid in readability and understanding. Any such numbering and lettering in itself is not intended to and should not be taken to indicate the ordering of elements and/or steps in the claims.

We claim:

1. A device for facilitating the treatment of chronic wounds or ulcerations on a user's limb or the user's foot, the device comprises:
a first insole constructed from semi compressed felt, wherein the semi compressed felt is made from cellulose and wool;
a cavity carved through the first insole, wherein the cavity is round in configuration, wherein a top surface of the cavity is beveled, and wherein the cavity in the first insole is configured to overlap the chronic wounds or the ulcerations on the user's limb or the user's foot;
an intermediate insole constructed from the semi-compressed felt;
a third sole constructed from semi-hardened plastic, wherein the third sole serves as permanent base for the device;
a compression sock that is equipped with a zipper;
wherein the compression sock equipped with the zipper is detachably attached to a top surface of the third sole with low adhering adhesive; and
wherein the compression sock has a compressive strength of about 10-50 mmHG.

2. The device of claim 1, wherein the semi-hardened plastic includes Ethylene Vinyl Acetate (EVA).

3. The device of claim 1, wherein the first insole and the intermediate insole are moisture and fluid absorbent and provide self-aeration, wherein the self-aeration comprises about 29% oxygen from air, and wherein the oxygen is configured to help in recovery of the chronic wounds or the ulcerations.

4. The device of claim 1, wherein the beveled cavity is configured to reduce stress around the chronic wounds or the ulcerations on the user's limb or the user's foot.

5. The device of claim 4, wherein the cavity is configured to allow flow of drainage or extrude from the chronic wounds or the ulcerations of the user's limb or the user's foot through the cavity;
the intermediate insole is configured to collect and absorb the drainage or extrude; and
wherein the first insole and the intermediate insole are changed periodically.

6. The device of claim 1, wherein the compression sock is ankle or knee-high sock.

7. The device of claim 6, wherein the zipper is configured to facilitate placement of the intermediate insole and the first insole along with the user's limb or the user's foot in the compression sock.

8. A method for facilitating a treatment process for chronic wounds or ulcerations of a user's limb or user's foot, the treatment process comprising the steps of:
   constructing a first insole from a semi-compressed felt,
   carving a cavity in the first insole configured to overlap chronic wounds or ulcerations on a user's limb or the user's foot;
   constructing an intermediate insole from the semi-compressed felt;
   constructing a third sole from Ethylene Vinyl Acetate, wherein the third sole serves as a permanent base for the device;
   equipping a compression sock with a zipper;
   detachably attaching the compression sock equipped with the zipper to a top surface of the third sole with a low adhering adhesive;
   placing the intermediate insole inside the compression sock equipped with the zipper;
   placing the first insole on top of the intermediate sole;
   securing the compression sock equipped with the zipper to a user's limb or the user's foot.

* * * * *